(12) United States Patent
Kilgore et al.

(10) Patent No.: US 6,834,437 B1
(45) Date of Patent: Dec. 28, 2004

(54) FOOT MEASUREMENT SYSTEM

(75) Inventors: Bruce J. Kilgore, Lake Oswego, OR (US); Christopher Cook, Portland, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 10/159,961

(22) Filed: May 29, 2002

(51) Int. Cl.⁷ .................... A43D 1/02; A61B 5/107
(52) U.S. Cl. ............................ 33/515; 33/3 B
(58) Field of Search ...................... 33/515, 512, 1 V, 33/3 R, 3 B, 1 C, 121

(56) References Cited

U.S. PATENT DOCUMENTS

| | | | | |
|---|---|---|---|---|
| 115,761 A | * | 6/1871 | McNichol | 33/3 R |
| 546,287 A | * | 9/1895 | Adler | 33/3 R |
| 770,065 A | | 9/1904 | Hertzler et al. | |
| 1,568,072 A | | 1/1926 | Krueger et al. | |
| 1,837,809 A | | 12/1931 | Delhaye | |
| 2,507,032 A | | 5/1950 | Mantos | |
| 2,522,899 A | | 9/1950 | Schlaugh et al. | |
| 2,942,344 A | * | 6/1960 | Brannock | 33/3 B |
| 3,438,134 A | * | 4/1969 | Schunk | 33/515 |
| 3,457,647 A | * | 7/1969 | Cohen | 33/3 R |
| 3,579,837 A | * | 5/1971 | Soriano | 33/3 B |
| 4,520,581 A | | 6/1985 | Irwin et al. | |
| 4,635,366 A | * | 1/1987 | Fohrman et al. | 33/3 B |
| 5,101,568 A | * | 4/1992 | Ferragamo | 33/3 B |
| 5,164,793 A | | 11/1992 | Wolfersberger et al. | |
| 5,671,055 A | | 9/1997 | Whittlesey et al. | |
| 5,822,223 A | | 10/1998 | Genest | |
| 6,029,358 A | | 2/2000 | Mathiasmeier et al. | |
| 6,163,971 A | | 12/2000 | Humphries, Jr. et al. | |
| 6,192,593 B1 | | 2/2001 | Borchers et al. | |
| 6,226,881 B1 | * | 5/2001 | Landauer | 33/515 |
| 6,256,896 B1 | * | 7/2001 | Landauer | 33/512 |
| 6,331,893 B1 | * | 12/2001 | Brown et al. | 33/3 R |
| 2003/0033723 A1 | * | 2/2003 | Snook | |

OTHER PUBLICATIONS

One Step Ahead® Children's Home Shoe Sizer, copyright 2000.
The Genuine Brannock Device, downloaded from the Brannock website on Apr. 29, 2001 (7 pages total).

* cited by examiner

Primary Examiner—Christopher W. Fulton
(74) Attorney, Agent, or Firm—Banner & Witcoff, Ltd.

(57) ABSTRACT

The invention is a foot measurement system suitable for mailing to consumers. The primary components of the measurement system include a length portion for determining the length of the foot and a width portion for determining the width of the foot. The length portion and the width portion each include sliders that may be positioned in an abutting relationship with areas of the foot. When the sliders are properly positioned, foot dimensions may be determined by reference to scales on each of the length and width portions. The measurement system also includes a container, for receiving and supporting the length portion and the width portion, that is suitable for use as a shipping container. In addition the measurement system may include a calibration device for ensuring measurement accuracy and a register for recording measurements.

66 Claims, 6 Drawing Sheets

FOOT MEASUREMENT SYSTEM

BACKGROUND OF THE INVENTION

1. Field of the Invention

The present invention relates to a system for measuring foot dimensions. The invention concerns, more particularly, a lightweight foot measuring system, for determining a length and a width of a foot, that is suitable for mailing to consumers.

2. Description of Background Art

Although sizing systems for footwear are standardized, many individuals find that footwear sizes vary between manufacturers. Consequently, an individual who wears a first size of footwear from a first manufacturer may wear a second size of footwear from a second manufacturer, with both the first size and the second size providing the individual with a proper fit. The primary reason for inconsistencies between footwear sizes relates to the unique lasts utilized by manufacturers to produce footwear. In shaping lasts for the manufacture of mass-produced footwear, foot measurements from a broad spectrum of the population are utilized to derive a set of dimensions that theoretically comprise a statistically-average foot for each shoe size. The dimensions may include the overall length of the foot, width of the foot, height of the first digit, contour of the instep, and at least six girth measurements. The dimensions are then used by the manufacturer to shape a corresponding series of lasts. Variations between the lasts used by different manufacturers result in footwear with different fit properties. Accordingly, the size of footwear worn by an individual may vary depending upon the manufacturer that produced the footwear.

A significant portion of modern footwear sales are conducted via mail order through catalogs or the Internet. Mail order provides a convenient manner for individuals to purchase footwear, especially if specific brands or styles are not offered by merchants in the geographic locale of the individual. A recurring issue with regard to mail order footwear sales relates to sizing. When purchases are made at a retail footwear outlet, the individual is typically provided with the opportunity to test-fit footwear prior to the sale. In this manner, the individual is assured that the footwear will fit properly. When sales occur through mail order, however, the customer rarely has the opportunity to test-fit the footwear prior to placing the order. Consequently, the individual may be required to return the footwear and place a substitute order if the ordered size does not provide a proper fit.

Proper sizing is also an issue for team sales. Sporting organizations often acquire footwear from a common manufacturer, thereby assuring a uniform appearance among team members. In order to ensure that the proper size of footwear is ordered for each team member, foot measurements for each individual may be taken. A common foot measuring device is the Brannock Device, which is found in many conventional retail footwear outlets. The Brannock Device includes a fixed scale and two sliding scales. To determine foot size, the user compares readings from the fixed scale, which determines the overall length of the foot, and one of the sliding scales, which determines the position of the ball of the foot. The greater reading typically indicates foot size. In addition, foot width may be measured using the second sliding scale.

A common issue with foot measuring systems such as the Brannock Device relates back to inconsistencies in footwear sizes provided by different manufacturers. Although the Brannock Device is well-suited for use in retail footwear outlets to provide an approximate footwear size, the Brannock Device may not be accurate with respect to individual manufacturers, Accordingly, reliance upon the Brannock Device, or any other device not calibrated to a specific manufacturer, may result in orders of footwear that are improperly fitted.

In order to provide a measurement system that is calibrated to a specific manufacturer, many manufacturers provide foot sizing charts that may be downloaded from the Internet and printed. To use the charts, the individual aligns the foot with a scale on the chart and reads the appropriate size. Printable charts, however, may not be precisely calibrated due to inherent inaccuracies in the printing process. To adjust for the inaccuracies, instructions accompanying the chart often provide means for calibrating the chart. Accurate calibration, however, is often difficult to achieve. Also, printable charts are two-dimensional and generally have greater measurement error than three-dimensional devices that contact the foot on opposing sides, such as the heel and toe, for example.

BRIEF SUMMARY OP THE INVENTION

The present invention is directed to a measurement system for determining dimensions of a foot. The measurement system includes a length portion for measuring the length of the foot and a width portion for measuring the width of the foot.

Elements of the length portion include a length scale positioned parallel to a longitudinal centerline of the foot; a heel support for receiving and positioning a heel of the foot; and a length slider that is movably positionable with respect to the toes of the foot. The length slider has a first side and an opposite second side. The first side is positionable in an abutting relationship with the toes and the second side has a configuration by which the length of the foot is determinable by reference to a position of the second side in relation to the length scale.

Elements of the width portion include a width scale positioned transverse to the length portion and a pair of independently adjustable width sliders that are movably positionable with respect to sides of the foot. The width sliders each have a third side and an opposite fourth side. The third sides are positionable in an abutting relationship with the sides of the foot and one of the fourth sides has a configuration by which the width of the foot is determinable by reference to a position of the fourth side in relation to the width scale.

The measurement system includes a container that receives and supports the length portion and the width portion. The container may be a cardboard-style box that is suitable as a shipping container for the measurement system, thereby facilitating mailing of the system to individuals or sporting organizations.

Further components of the system include a calibration device and a register. The individual utilizes the calibration device to ensure that measurements are accurate by comparing measurements performed on the calibration device with predetermined dimensions of the calibration device. The register is utilized to record measurements such that individuals may subsequently recall the measurements when ordering footwear.

The various advantages and features of novelty that characterize the present invention are pointed out with particularity in the appended claims. To gain an improved understanding of the advantages and features of novelty that characterize the present invention, however, reference should be made to the descriptive matter and accompanying drawings which describe and illustrate preferred embodiments of the invention.

DETAILED DESCRIPTION OF THE INVENTION

Figure 1:
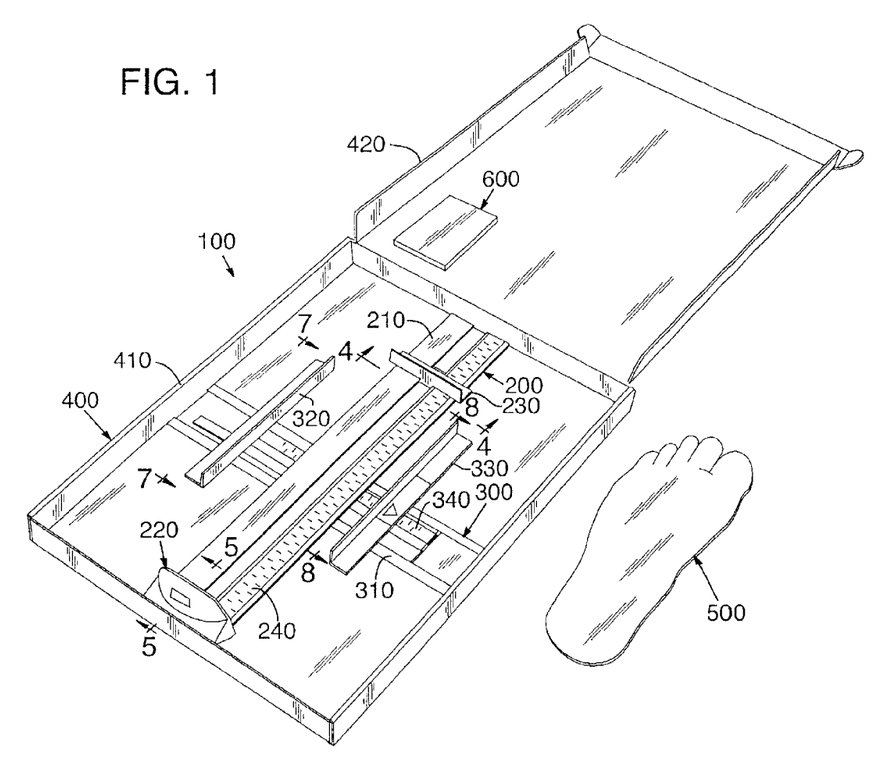
FIG. 1 is a perspective view of a foot measurement system in accordance with the present invention.
Figure 2:
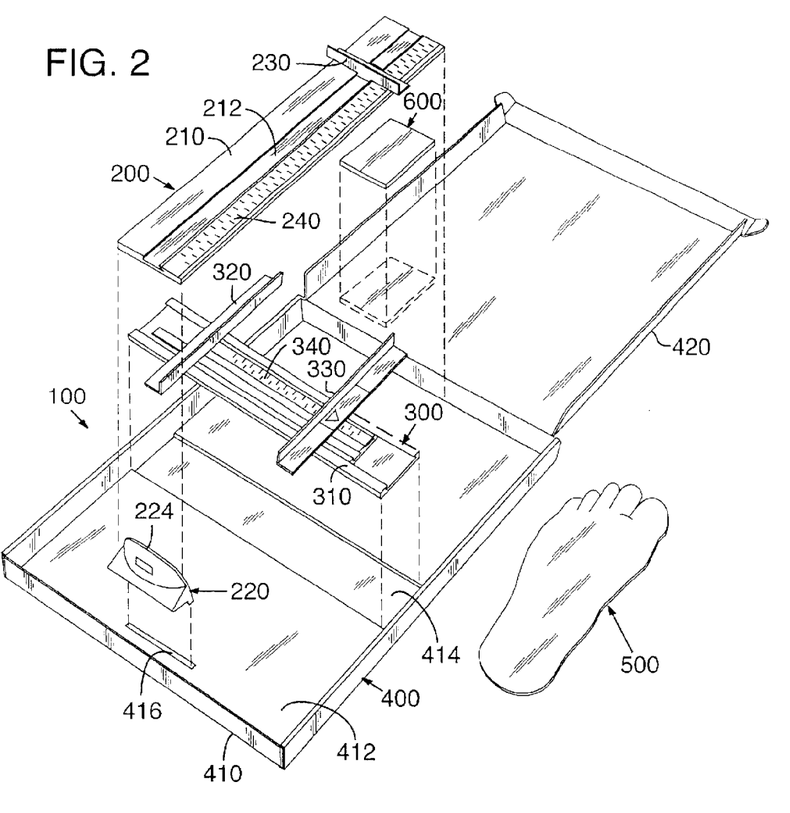
FIG. 2 is an exploded view of the measurement system depicted in FIG. 1.
Figure 3:
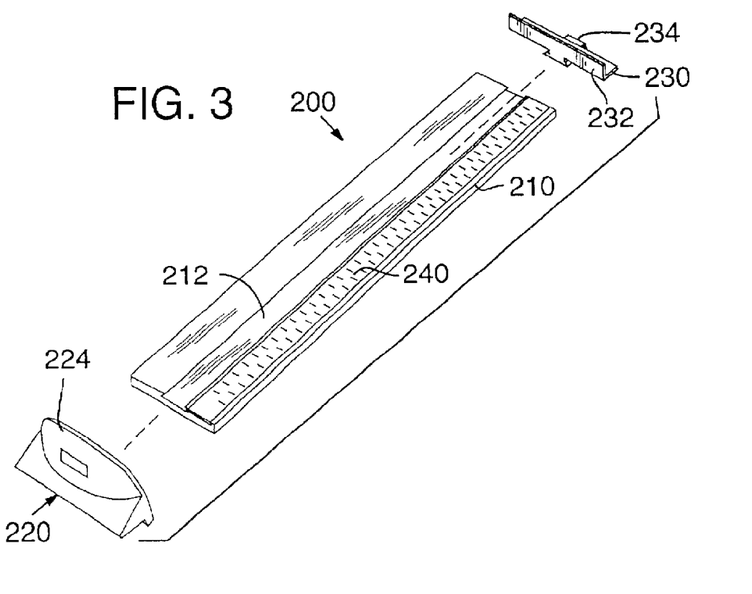
FIG. 3 is an exploded view of a length portion of the measurement system depicted in FIG. 1.
Figures 4, 5:
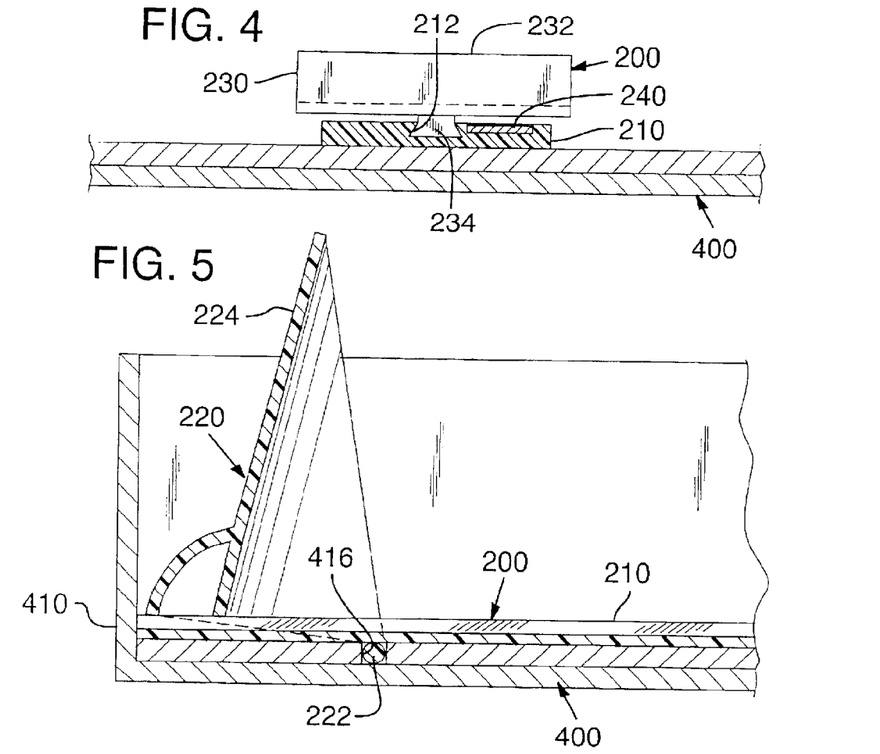
FIG. 4 is a cross-sectional view along line 4—4 in FIG. 1.
FIG. 5 is a cross-sectional view along line 5—5 in FIG. 1.
Figure 4A:
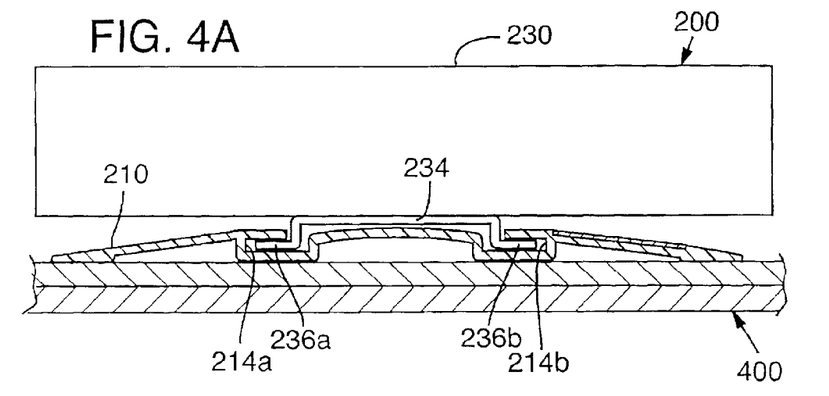
FIG. 4A is a cross-sectional view as taken along line 4—4 in FIG. 1 depicting an alternate channel configuration.
Figure 6:
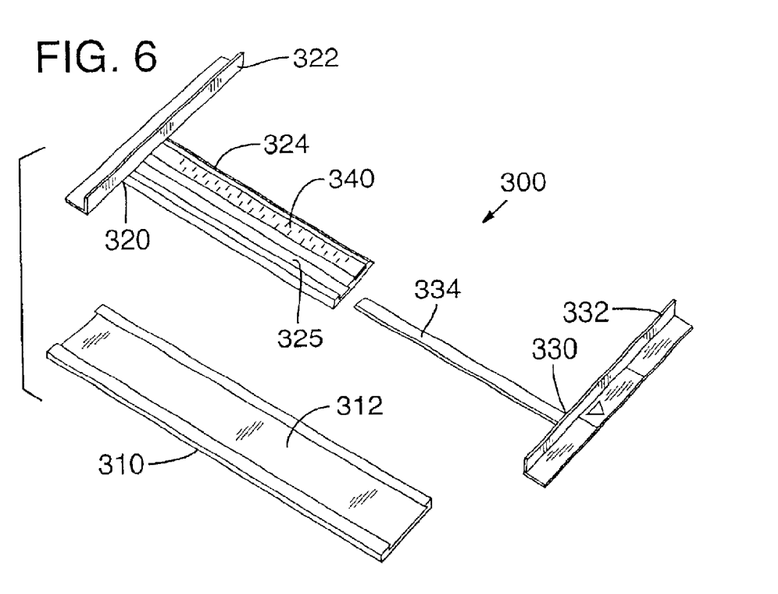
FIG. 6 is an exploded view of a width portion of the measurement system depicted in FIG. 1.

Referring to the figures, wherein like numerals indicate like elements, a foot measurement system 100 in accordance with the present invention is disclosed. The primary elements of measurement system 100, as depicted in FIGS. 1 and 2, are a length portion 200 for measuring a length of a foot and a width portion 300 for measuring a width of the foot. In addition, measurement system 100 includes a container 400 for receiving and supporting the various components of measurement system 100; a calibration device 500 for ensuring that measurement system 100 provides accurate foot dimensions; and a register 600 for recording measurements.

Measurement system 100 is particularly suited to individuals or sporting organizations that purchase footwear through mail order. Unlike many conventional foot measuring systems, measurement system 100 may be inexpensively manufactured and mailed to consumers because the various elements of length portion 200 and width portion 300 are constructed from lightweight materials, such as polymers, which may be quickly assembled. Furthermore, container 400 may be constructed from a cardboard-style box that serves as the shipping container. Consequently, measurement system 100 may be mailed to individuals or sporting organizations and used by the individuals or sporting organizations to ensure that ordered footwear is properly fitted to each individual. Following use, measurement system 100 may be retained by the consumer for a future use or disassembled and recycled.

Length portion 200 and width portion 300, depicted in FIGS. 3–8, operate to cooperatively measure the length and width of a foot. Length portion 200 includes a base 210, a heel support 220 located on an end of base 210, a length slider 230 that is movably positionable with respect to base 210 and heel support 220, and a length scale 240. Length portion 200 is positioned above and transverse to width portion 300. The primary components of width portion 300 are a base 310, a first slider 320, a second slider 330, and a width scale 340. Both first slider 320 and second slider 330 are movably positionable with respect to base 310 and each other.

Container 400 is configured to receive and support length portion 200 and width portion 300. The primary components of container 400 are a box portion 410 and a lid portion 420. Box portion 410 includes a bottom 412 with a recess 414 and a slot 416. Recess 414 is configured to receive base 310 of width portion 300 such that the upper surface of bottom 412 is approximately level with the upper surface of base 310. As noted, length portion 200 is positioned above and transverse to width portion 300. Accordingly, length portion 200 rests upon the upper surface of bottom 412 and crosses width portion 300, thereby forming the shape of a cross. Slot 416 receives a pivot bar 222 of heel support 220, as described below. Both length portion 200 and width portion 300 may be attached to container 400 through any suitable means, including rivets, friction fit, or adhesive bonding.

The individual components of length portion 200 and width portion 300 will now be discussed in greater detail. As noted, the primary elements of length portion 200 are base 210, heel support 220, length slider 230, and length scale 240. Base 210 is a generally planar member with an upper surface that includes a channel 212 for receiving length slider 230. Channel 212 may have a dovetail configuration that mates with a corresponding dovetail configuration formed in length slider 230, as described below and depicted in FIG. 4. Base 210 may also include a shallow indentation in a parallel alignment with channel 212 that receives length scale 240.

Heel support 220 is a generally concave structure located on an end of base 210 that provides a secure location for positioning the heel when measuring the foot. In order to ensure that the measurements are both accurate and consistent, the position of heel support 220 should be fixed relative to scale 240. Accordingly, heel support 220 may be attached to base 210 or container 400. As depicted in the figures, heel support 220 may include a pivot bar 222, which extends under base 210 and is received by slot 416 of container 400, and a heel cup 224 that receives the heel. Slot 416 ensures that the position of heel support 220 is fixed, but permits heel support 220 to rotate forward, thereby reducing the profile height of heel support 220 during shipping or when lid portion 420 of container 400 is closed. The receipt of pivot bar 222 in slot 416 also serves to secure base 210 in position within container 400.

Length slider 230 includes a toe stop 232 that is attached to an insert 234. Toe stop 232 is a generally L-shaped member with a vertical portion and a horizontal portion. The vertical portion of toe stop 232 is configured to abut the toes when length slider 230 is positioned to measure the length of the foot. The horizontal portion of length slider 230 is configured to extend forward of the toes and may include directions on how to read length scale 240 in order to accurately determine the length of the foot. Insert 234 extends from the lower surface of toe stop 232 and is received by channel 212 of base 210. As noted, channel 212 may have a dovetail configuration. Accordingly, insert 234 may have a corresponding configuration that mates with channel 212 and slides within channel 212, thereby facilitating movement of length slider 230 along base 210. Toe stop 232 and insert 234 may be integrally-formed, or separately-formed and attached with an adhesive or thermo-bonding process, for example. In an alternate embodiment, depicted in FIG. 4A, channel 212 is formed of two grooves 214a and 214b formed in base 210. Insert 234 of length slider 230, therefore, includes two tabs 236a and 236b that are received by grooves 214 and slide within grooves 214.

Length scale 240 is used to determine the length of the foot and should be positioned such the position of length slider 230 indicates the length of the foot. As noted, base 210 may include a shallow indentation that receives length scale 240. Alternately, length scale 240 may be positioned adjacent to base 210 or in any other position that facilitates a determination of foot length. Length scale 240 may be printed on an adhesive paper that is then positioned and attached to base 210 or etched into the surface of base 210, for example.

As noted, the primary elements of width portion 300 are base 310, first slider 320, second slider 330, and width scale 340. In general, first slider 320 and second slider 330 are independently adjustable such that each may be brought into contact with opposite sides of the foot. Base 310, a generally planar member, is positioned within recess 414 of container 400 and includes a channel 312 formed in the upper surface. Channel 312 receives first slider 320 and may have a dovetail configuration.

First slider 320 includes a first width stop 322 that is placed in an abutting position with a first side of the foot when measuring width, an insert 324 that is positioned within channel 312, and a spacer 326 disposed between first width stop 322 and insert 324. First width stop 322 has a generally L-shaped configuration with a vertical portion and a horizontal portion. The vertical portion of first width stop 322 is configured to abut the first side of the foot when determining the width of the foot. The horizontal portion of first width stop 322 is attached to spacer 326. Insert 324 is a generally planar member that is configured to slide within channel 312 of base 310. As noted, channel 312 may have a dovetail configuration. Accordingly, insert 324 may have a corresponding configuration that secures first slider 320 to base 310, but permits side-to-side translation when positioning first slider 320. Insert 324 includes a guideway 325, also with a dovetail configuration, in an upper surface that receives second slider 330, as described below. Spacer 326 is disposed between first width stop 322 and insert 324. The upper surface of base 310 generally corresponds with the upper surface of bottom 412 of container 400. Spacer 326, therefore, raises the elevation of first width stop 322 to prevent first width stop 322 from making significant contact with base 310 and bottom 412.

Second slider 330 includes a second width stop 332 that is placed in an abutting position with a second side of the foot when measuring width, an insert 334 that is positioned within guideway 325 of insert 324, and a spacer 336 disposed between second width stop 332 and insert 334. Second width stop 332 has a generally L-shaped configuration with a vertical portion and a horizontal portion. The vertical portion of second width stop 332 is configured to abut the second side of the foot when taking measurements. The horizontal portion of second width stop 332 is attached to spacer 336 and may include directions on how to read width scale 340 in order to determine the width of the foot. Insert 334 is configured to slide within guideway 325 of insert 324. As noted, guideway 325 may have a dovetail configuration. Accordingly, insert 334 may have a corresponding dovetail configuration that secures second slider 330 to first slider 330, but permits side-to-side translation when positioning second slider 330. Note that this configuration permits first slider 320 and second slider 330 to move independently. Spacer 336, which performs a function similar to spacer 326, raises the elevation of second width stop 332 to prevent second width stop 332 from making significant contact with base 310 and bottom 412.

Figure 7:
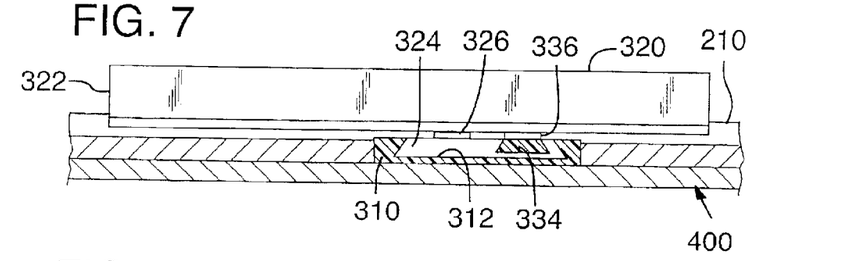
FIG. 7 is a cross-sectional view along line 7—7 in FIG. 1.
Figure 7A:
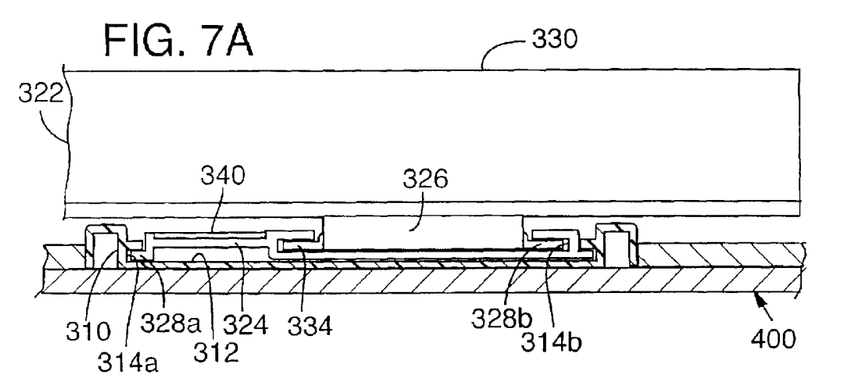
FIG. 7A is a cross-sectional view as taken along line 7—7 in FIG. 1 depicting an alternate channel configuration.
Figure 8:
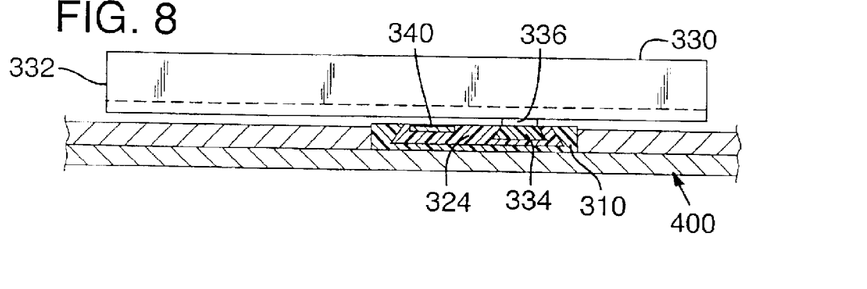
FIG. 8 is a cross-sectional view along line 8—8 in FIG. 1.
Figure 8A:
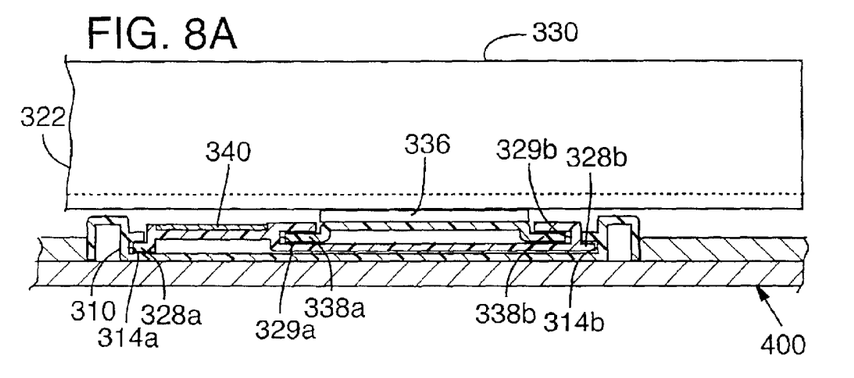
FIG. 8A is a cross-sectional view as taken along line 8—8 in FIG. 1 further depicting the alternate channel configuration of FIG. 7A.

In an alternate embodiment, depicted in FIGS. 7A and 8A, base 310 is formed to have two grooves 314a and 314b. First slider 320 includes, therefore, two corresponding tabs 328a and 328b that are received by grooves 314 and slide within grooves 314. First slider 320 also includes two additional grooves 329a and 329b that receive tabs 338 of second slider 330. This configuration operates in a manner that also permits first slider 320 and second slider 330 to move independently.

Width scale 340 may be positioned on insert 324 and adjacent to guideway 325, or in any other position that facilitates a determination of foot width. Width scale 340 may be printed on an adhesive paper that is then positioned and attached to base 310 or etched into the surface of base 310, for example.

Traditional foot measuring devices measure the foot in accordance with one or more standard sizing systems. For example, the standard system for measuring men's feet in the United States correlates a size eleven to a foot with an eleven inch length, and each full size differs by one-third of an inch. A size 8, therefore, correlates to a foot with a 10 inch length. Furthermore, width in the standard U.S. system is measured using an alphabetical scale. Scales 240 and 340 may be configured to measure the foot according to one or more standard systems or may be configured to measure the foot in accordance with a non-standard system, such as by inches or centimeters, that is developed to meet specific needs of the manufacturer. As noted in the Description of Background Art section, the size of footwear worn by an individual may vary depending upon the manufacturer that produced the footwear. By correlating scales 240 and 340 with a standard sizing system, individuals or sporting organizations may be led to believe that measurement system 100 properly determines footwear sizes for a variety of manufacturers, thereby leading to improper fit. A non-standard system therefore has the benefit of ensuring that foot measurements, as determined by measurement system 100, are relayed to the manufacturer, thereby providing the manufacturer with the exclusive opportunity to determine which footwear size will provide the most proper fit. In order to make this determination, the manufacturer may draw upon many sources of information, including precise knowledge of footwear dimensions and a wealth of experience regarding fit for various foot dimensions.

Figure 9:
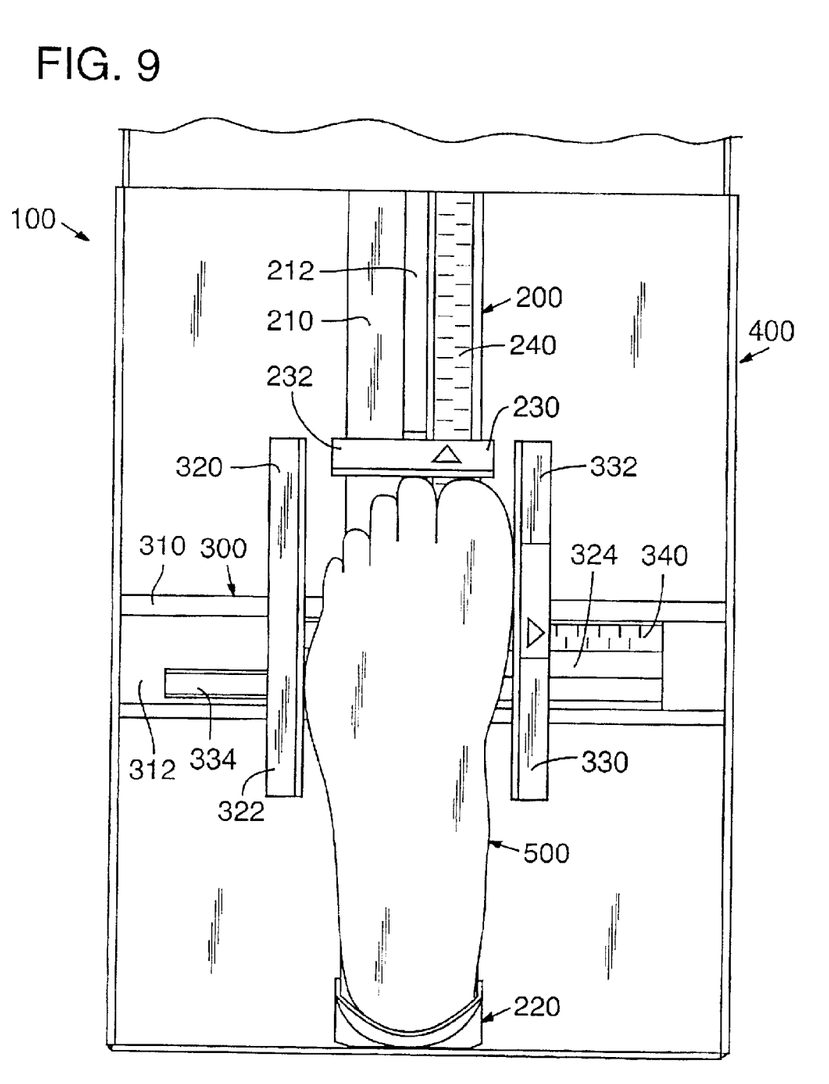
FIG. 9 is a plan view of the measurement system.

Measurements are taken by positioning the foot along the longitudinal axis of base 210 such that the heel is located in heel support 220. Length slider 230 is then positioned such that a first side of toe stop 232 is in an abutting relationship with the toes. The length of the foot may then be determined from length scale 240 by reference to the opposite, second side of length slider 230. To assist the individual when measuring length, an arrow or other directions may be located on toe stop 232, as depicted in FIG. 9, to indicate that readings should be taken from the second side of toe stop 232. Alternatively, length portion 200 may be configured such that measurements are taken from the first side of toe stop 232, but the length of the foot may be more difficult to determine when the foot obscures portions of length scale 240. With regard to width, sliders 320 and 330 are positioned adjacent opposite sides of the foot and the width of the foot may be read from width scale 340 in reference to the side of second width stop 332 located opposite the foot. The measurement process may then be repeated for the opposite foot.

Suitable materials for length portion 200, width portion 300, and container 400 may vary depending upon the projected number of individuals that may utilize measuring system 100, the preferred weight of measuring system 100, and the desired durability of measuring system 100. In addition, a measuring system 100 that is intended for use by adults may be formed of heavier, more durable materials than a measuring system 100 that is intended for use by children. Although length portion 200 and width portion 300 may be formed of materials such as steel, aluminum, or composites of a polymer and high-strength fibers, suitable durability and weight are achieved with polymer materials such as acrylonitrile butadiene styrene, acrylic, polycarbonate, and high impact polystyrene. Similar materials may also be used for container 400, including cardboard or other lightweight materials such as polystyrene, polypropylene, and polyethylene.

Container 400 often includes various surfaces on which information regarding the use or care of measurement system 100 may be printed. As noted, container 400 may include bottom 412 and lid portion 420, both typically having interior and exterior surfaces. The types of information that may be displayed on these surfaces include step-by-step directions on how to measure the foot with measuring system 100, diagrams that correspond with the various steps, identifying information or indicia of the manufacturer, information on how to order from the manufacturer, and directions concerning the use of calibration device 500 and register 600. In addition, register 600 may be attached to one of the surfaces.

Accuracy may be compromised if measurement system 100 is damaged during shipping or during use, for example. Calibration device 500 provides a convenient method for an individual to check the accuracy of measurement system 100. Generally, calibration device 500 is an element having a predetermined length and width. To check the accuracy of measurement system 100, calibration device 100 is positioned within heel support 220 and along the longitudinal axis of base 210, as depicted in FIG. 9. Sliders 230, 320, and 330 are positioned in an abutting relationship with calibration device 500 and both length and width are read. The measured length and width are then compared to the predetermined length and width of calibration device 500. If the measurements correspond, measurement system 100 is accurately calibrated. If, however, the measurements do not correspond, then the individual may be required to adjust foot measurements by the difference to achieve accurate results. Accordingly, calibration device 500 not only permits the accuracy of measurement system 100 to be checked, but also provides a system by which inaccuracies may be corrected.

Register 600 may be used to record measurements once accurate measurements of a foot are made. Generally, register 600 may be any device or method that facilitates the recording of measurements. As depicted in FIGS. 1 and 2, register 600 is a pad of preprinted pages, each page including spaces for recording the length and width of each foot. Sporting organizations often require footwear for a plurality of individuals. Once readings are taken for a specific individual, the readings may be recorded on one of the preprinted pages of register 600. The preprinted page may then be removed from the pad, thereby exposing a new preprinted page, and the printed page with the recorded readings may be given to the individual. The process may be repeated for subsequent individuals. Each individual may then utilize the recorded dimensions to independently order footwear from the manufacturer that provides a proper fit.

The present invention is disclosed above and in the accompanying drawings with reference to a variety of preferred embodiments. The purpose served by disclosure of the preferred embodiments, however, is to provide an example of the various aspects embodied in the invention, not to limit the scope of the invention. One skilled in the art will recognize that numerous variations and modifications may be made to the preferred embodiments without departing from the scope of the present invention, as defined by the appended claims.

That which is claimed is:

1. A measurement system for determining dimensions of a foot, said measurement system comprising:
    a length portion for measuring a length of the foot, said length portion having components that include:
        a length scale positioned relative to a longitudinal centerline of the foot,
        a heel support for receiving and securely positioning a heel of the foot, and
        a length slider that is movably positionable in a direction of the longitudinal centerline of the foot, said length slider being positionable in an abutting relationship with toes of the foot to measure the length of the foot; and
    a width portion for measuring a width of the foot, said width portion having components
    that are separate from said components of said length portion and include:
        a width scale positioned transverse to said length scale, and
        a pair of independently adjustable width sliders that are movably positionable with respect to medial and lateral sides of the foot and in a direction that is transverse to said length scale, said width sliders being positionable in an abutting relationship with the sides of the foot to measure the width of the foot.

2. The measurement system of claim 1, wherein said length portion and said width portion are incorporated into a container.

3. The measurement system of claim 2, wherein said container includes a lid portion, a bottom portion, and at least one wall portion that extends between said bottom portion and said lid portion.

4. The measurement system of claim 3, wherein said container is a cardboard-style box.

5. The measurement system of claim 3, wherein an upper surface of said bottom portion includes a recessed area for receiving said width portion.

6. The measurement system of claim 5, wherein said length portion is located on said upper surface of said bottom portion and positioned transverse to said width portion, said length portion thereby crossing over said width portion.

7. The measurement system of claim 5, wherein said width portion includes a base, said base being located within said recess, and an upper surface of said base being substantially located on a plane of said upper surface of said bottom portion.

8. The measurement system of claim 3, wherein said bottom portion includes a slot for receiving a pivot bar of said heel support, said pivot bar forming a pivot point for said heel support, said heel support being pivotable to a vertical position and pivotable to a horizontal position, a height of said heel support in said horizontal position being less than a height of said wall portion.

9. The measurement system of claim 8, wherein said heel support includes a heel cup for contacting the heel, said pivot bar and said heel cup being positioned on opposite sides of a base of said length portion.

10. The measurement system of claim 1, wherein said length portion includes a base, said base having a channel for receiving an insert of said length slider, said insert being movably positionable within said channel.

11. The measurement system of claim 10, wherein said channel and said insert each have corresponding dovetail configurations.

12. The measurement system of claim 1, wherein said width portion includes a base, said base having a channel for receiving a first insert of a first of said width sliders, said first insert being movably positionable within said channel.

13. The measurement system of claim 12, wherein said channel and said first insert each have corresponding dovetail configurations.

14. The measurement system of claim 12, wherein said first insert includes a guideway, said guideway receiving a second insert of a second of said width sliders, said second insert being movably positionable within said guideway.

15. The measurement system of claim 1, wherein said measurement system includes a calibration device with predetermined dimensions, said calibration device being positionable between said heel support and said length slider and between said width sliders to determine an accuracy of said system.

16. The measurement system of claim 15, wherein said calibration device has a configuration that generally corresponds with a shape of a human foot.

17. The measurement system of claim 1, wherein said measurement system includes a register for recording the dimensions of the foot.

18. The measurement system of claim 17, wherein said register is a plurality of individual, removable pages upon which the dimensions of the foot may be written.

19. The measurement system of claim 1, wherein said length slider includes a first side and an opposite second side, said first side being positionable in an abutting relationship with the toes of the foot, the length of the foot being determined by reference to a position of said second side in relation to said length scale.

20. The measurement system of claim 1, wherein said width sliders each include a third side and an opposite fourth side, said third sides being positionable in an abutting relationship with the sides of the foot, the width of the foot being determined by reference to one of said fourth sides in relation to said width scale.

21. A measurement system for determining at least one dimension of a foot, said measurement system comprising:
   base with a channel located in said base;
   a first slider having a first stop located outside said channel and a first insert located within said channel, said first stop being attached to said first insert such that said first slider is movably positionable along said channel and configured to abut a first portion of the foot, said first insert including a guideway located in said first insert;
   a second slider having a second stop located outside said guideway and a second insert located within said guideway, said second stop being attached to said second insert such that said second slider is movably positionable along said guideway and configured to abut a second portion of the foot, said second portion being located opposite said first portion, and said second stop having a configuration by which the one dimension of the foot is determinable by reference to a position of said second stop in relation to a scale located on one of said sliders.

22. The measurement system of claim 21, wherein said channel and said first insert each have corresponding dovetail configurations.

23. The measurement system of claim 21, wherein said guideway and said second insert each have corresponding dovetail configurations.

24. The measurement system of claim 21, wherein said measurement system includes a calibration device with predetermined dimensions, said calibration device being positionable between said first slider and said second slider to determine an accuracy of said system.

25. The measurement system of claim 24, wherein said calibration device has a configuration that generally corresponds with a shape of a human foot.

26. The measurement system of claim 21, wherein said measurement system includes a register for recording the at least one dimension of the foot.

27. The measurement system of claim 26, wherein said register is a plurality of individual, removable pages upon which the at least one dimension of the foot may be written.

28. The measurement system of claim 21, wherein said base, said first slider, and said second slider comprise a width portion of said measurement system and are configured to determine a width of the foot.

29. The measurement system of claim 28, wherein said measurement system includes a length portion for determining a length of the foot, said length portion including:
   a length scale positioned parallel to a longitudinal centerline of the foot,
   a heel support for receiving and positioning a heel of the foot, and
   a length slider that is movably positionable with respect to said length scale.

30. The measurement system of claim 29, wherein said length slider includes a first side and an opposite second side, said first side being positionable in an abutting relationship with the foot, the length of the foot being determined by reference to a position of said second side in relation to said length scale.

31. The measurement system of claim 29, wherein said length portion includes a base, said base having a channel for receiving an insert of said length slider, said insert being movably positionable within said channel.

32. The measurement system of claim 29, wherein said length portion and said width portion are incorporated into a container.

33. The measurement system of claim 32, wherein said container includes a lid portion, a bottom portion, and at least one wall portion that extends between said bottom portion and said lid portion.

34. The measurement system of claim 33, wherein said container is a cardboard-style box.

35. The measurement system of claim 33, wherein an upper surface of said bottom portion includes a recessed area for receiving said width portion.

36. The measurement system of claim 35, wherein said length portion is located on said upper surface of said bottom portion and positioned transverse to said width portion, said length portion thereby crossing over said width portion.

37. The measurement system of claim 35, wherein said base of said width portion is located within said recess, and an upper surface of said base is substantially located on a plane of said upper surface of said bottom portion.

38. The measurement system of claim 33, wherein said bottom portion includes a slot for receiving a pivot bar of said heel support, said pivot bar forming u pivot point for said heel support, said heel support being pivotable to a vertical position and pivotable to a horizontal position, a height of said heel support in said horizontal position being less than a height of said wall portion.

39. The measurement system of claim 38, wherein said heel support includes a heel cup for contacting the heel, said pivot bar and said heel cup being positioned on opposite sides of a base of said length portion.

40. A measurement system for determining dimensions of a foot that do not include a heel-to-ball dimension, said measurement system comprising:
 a length portion for measuring a length of the foot, said length portion including a length base, a heel support located on an end of said length base, a length slider movably positionable with respect to said length base, and a length scale located on said length base;
 a width portion for measuring a width of the foot, said width portion having components that are separate from components of said length portion, and said width portion including a width base, a pair of width sliders that are independently and movably positionable with respect to said width base and in a direction that is transverse to said length scale, and a width scale located on one of said width sliders; and
 a container, said length portion and said width portion being received by said container and attached to said container.

41. The measurement system of claim 40, wherein said container includes a bottom portion and wall portions extending upward from said bottom portion to define a cavity within said container for receiving said length portion and said width portion.

42. The measurement system of claim 41, wherein a recess is formed in an upper surface of said bottom portion, one of said length base or said width base being located in said recess, and the other of said length base or said width base being located transverse to said recess and on said upper surface of said bottom portion.

43. The measurement system of claim 42, wherein said width base is located in said recess and said length base is located on said upper surface of said bottom portion, said length base thereby crossing over said width base.

44. The measurement system of claim 43, wherein an upper surface of said width base is substantially located on a plane of said upper surface of said bottom portion.

45. The measurement system of claim 41, wherein said container includes a lid portion.

46. The measurement system of claim 41, wherein said bottom portion includes a slot for receiving a pivot bar of said heel support, said pivot bar forming a pivot point for said heel support, said heel support being pivotable to a vertical position and pivotable to a horizontal position, a height of said heel support in said horizontal position being less than a height of said wall portion.

47. The measurement system of claim 46, wherein said heel support includes a heel cup for contacting the heel, said pivot bar and said heel cup being positioned on opposite sides of said length base.

48. The measurement system of claim 41, wherein said container is a cardboard-style box.

49. The measurement system of claim 40, wherein said length base includes a channel for receiving an insert of said length slider, said insert being movably positionable within said channel.

50. The measurement system of claim 49, wherein said channel and said insert each have corresponding dovetail configurations.

51. The measurement system of claim 40, wherein said width base includes a channel for receiving a first insert of a first of said width sliders, said first insert being movably positionable within said channel.

52. The measurement system of claim 51, wherein said channel and said first insert each have corresponding dovetail configurations.

53. The measurement system of claim 51, wherein said first insert includes a guideway, said guideway receiving a second insert of a second of said width sliders, said second insert being movably positionable within said guideway.

54. The measurement system of claim 40, wherein said measurement system includes a calibration device with predetermined dimensions, said calibration device being positionable between said heel support and said length slider and between said width sliders to determine an accuracy of said system.

55. The measurement system of claim 54, wherein said calibration device has a configuration that generally corresponds with a shape of a human foot.

56. The measurement system of claim 40, wherein said measurement system includes a register for recording dimensions of the foot.

57. The measurement system of claim 56, wherein said register is a plurality of individual, removable pages upon which the dimensions of the foot may be written.

58. A measurement system for determining dimensions of a foot, said measurement system comprising:
 a length portion for measuring a length of the foot, said length portion including a length base, a heel support located on an end of said length base, a length slider movably positionable with respect to said length base, and a length scale located on said length base, the length of the foot being determinable by reference to a position of said length slider in relation to said length scale;
 a width portion for measuring a width of the foot, said width portion including a width base having a channel formed therein, a first width slider and a second width slider that are independently and movably positionable with respect to each other, and a width scale located on one of said width sliders, said first slider having a first stop located outside said channel and a first insert located within said channel, said first stop being attached to said first insert such that said first slider is movably positionable along said channel and configured to abut a first side portion of the foot, said first insert including a guideway located in said first insert, said second slider having a second stop located outside said guideway and a second insert located within said guideway, said second stop being attached to said second insert such that said second slider is movably positionable along said guideway and configured to abut a second side portion of the foot, said second side portion being located opposite said first side portion, and said second stop having a configuration by which the width of the foot is determinable by reference to a position of said second stop in relation to said width scale; and
 a container that includes a bottom portion, a lid portion, and wall portions located between said bottom portion and said lid portion to define a cavity within said container for receiving said length portion and said width portion, an upper surface of said bottom portion including a recess, one of said length base or said width base being located in said recess, and the other of said length base or said width base being located transverse to said recess and on said upper surface of said bottom portion.

59. The measurement system of claim 58, wherein said bottom portion includes a slot for receiving a pivot bar of said heel support, said pivot bar forming a pivot point for said heel support, said heel support being pivotable to a vertical position and pivotable to a horizontal position, a height of said heel support in said horizontal position being less than a height of said wall portion.

60. The measurement system of claim 59, wherein said heel support includes a heel cup for contacting the heel, said pivot bar and said heel cup being positioned on opposite sides of a base of said length portion.

61. The measurement system of claim 58, wherein said channel and said first insert each have corresponding dovetail configurations.

62. The measurement system of claim 58, wherein said guideway and said second insert each have corresponding dovetail configurations.

63. The measurement system of claim 58, wherein said measurement system includes a calibration device with predetermined dimensions, said calibration device being positionable between said heel support and said length slider and between said width sliders to determine an accuracy of said system.

64. The measurement system of claim 63, wherein said calibration device has a configuration that generally corresponds with a shape of a human foot.

65. The measurement system of claim 58, wherein said measurement system includes a register for recording dimensions of the foot.

66. The measurement system of claim 65, wherein said register is a plurality of individual, removable pages upon which the dimensions of the foot may be written.

* * * * *